(12) United States Patent
Chen et al.

(10) Patent No.: US 8,453,376 B2
(45) Date of Patent: Jun. 4, 2013

(54) FULL SPECTRUM SUNSHINE SIMULATION APPARATUS FOR DEVELOPING BIOLOGICAL GROWTH

(75) Inventors: Kai-Hsien Chen, Taipei (TW); Wen-Ho Chen, Hsinchu (TW)

(73) Assignees: Sinetics Associates International Taiwan Ltd., Taipei County (TW); J.S. Technology Co., Ltd., Hsinchu (TW)

( * ) Notice: Subject to any disclaimer, the term of this patent is extended or adjusted under 35 U.S.C. 154(b) by 471 days.

(21) Appl. No.: 12/781,189

(22) Filed: May 17, 2010

(65) Prior Publication Data

US 2010/0287830 A1  Nov. 18, 2010

(30) Foreign Application Priority Data

May 18, 2009  (TW) ................................ 98208608 U (51) Int. Cl.
  *A01G 9/02*  (2006.01)
(52) U.S. Cl.
  USPC .................................................... 47/58.1 LS
(58) Field of Classification Search
  USPC .................................. 47/1.01 R, 58.1 LS, 60
  See application file for complete search history.

(56) References Cited

U.S. PATENT DOCUMENTS

| | | | | |
|---|---|---|---|---|
| 4,914,858 A * | 4/1990 | Nijssen et al. | ............. | 47/1.01 R |
| 5,012,609 A * | 5/1991 | Ignatius et al. | ............. | 47/1.01 R |
| 5,946,852 A * | 9/1999 | Oram et al. | ................ | 47/58.1 R |
| 6,554,450 B2 * | 4/2003 | Fang et al. | ..................... | 362/231 |
| 6,725,598 B2 * | 4/2004 | Yoneda et al. | ..................... | 47/60 |
| 7,160,717 B2 * | 1/2007 | Everett | ........................ | 435/286.2 |
| 7,617,057 B2 * | 11/2009 | May et al. | ........................ | 702/62 |
| 2001/0047618 A1 * | 12/2001 | Fang et al. | ..................... | 47/65.5 |
| 2009/0207604 A1 * | 8/2009 | Robotham | ..................... | 362/230 |
| 2010/0287830 A1 * | 11/2010 | Chen et al. | ................ | 47/58.1 LS |

FOREIGN PATENT DOCUMENTS

TW  M323194  12/2007

* cited by examiner

*Primary Examiner* — Frank T Palo
(74) *Attorney, Agent, or Firm* — Rosenberg, Klein & Lee (57) ABSTRACT

Disclosed is a full spectrum sunshine simulation apparatus for developing biological growth which comprises a full spectrum light emitting diode module and a photoperiod controller. Therein, the full spectrum light emitting diode module includes a printed circuit board and a plurality of full spectrum light emitting diodes, wherein the luminescence spectrum of the full spectrum light emitting diodes has a wavelength range of 350 nm to 800 nm. The photoperiod controller, connected to the full spectrum light emitting diode module, is in charge of lighting periods of the plurality of full spectrum light emitting diodes, color temperatures and emitting angles of the lights emitted from the plurality of full spectrum light emitting diodes, thereby simulating a environment under artificial sunlight.

11 Claims, 8 Drawing Sheets

FULL SPECTRUM SUNSHINE SIMULATION APPARATUS FOR DEVELOPING BIOLOGICAL GROWTH

BACKGROUND OF THE INVENTION

1. Field of the Invention

The invention relates to a natural environment simulation apparatus for controlling biological responses, in particular, to an artificial lighting apparatus functioning by simulating full spectrum sunshine for developing biological growth.

2. Description of Related Art

The plants are capable of capturing photon energy to perform photosynthesis which supports the living beings on earth. In addition, plants also contain photon capture apparatus called photoreceptors which response to different wavelengths of lights and control growth and development of plant. The most well known phtoreceptor is phytochrome which responds to red light and far-red light in regulating many important physiological responses including the germination of seeds and controlling the time of flowering. The phytochromes have two forms $P_R$ (which absorbs red light) and $P_{FR}$ (which absorbs far-red light). Many plant physiological responses like flowering and germination of seed are reversibly controlled by shinning red light and far-red light. This photoreversibility is caused by the interconvertability of the two forms $P_R$ and $P_{FR}$. Additionally, some plants growth is influenced by the length of day and night, i.e., called as photoperiodism. The photoperiodism is used to regulate the formation and quantity of phytochrome within the plants and to set circadian rhythms.

In the genetic sequencing of CRY1 gene and the following studies, another short wavelength photoreceptor is cryptochrome has been discovered, which also controls *Arabidopsis thaliana* stem elongation, folia unfolding, photoperiod flowering, and other biological clock response. In addition, a blue light photoreceptor phototropin has been correlated with phototropism. In nature, these different wavelengths of lights are composed as one and expressed as different color temperatures followed by the sunrise from the east and set to the west. The traditional artificial lighting and growth chamber cannot change of light angles and color temperatures in the continuous way just as the sun does. This makes it difficult to study and control the plant growth and development through these photoreceptors in the nature sun or simulate the sun fashion.

Please refer to Taiwan Patent No. M323194, "Multifunctional light emitting diode plant cultivation lamp for promoting growth rate", which is characterized in that the ratio of composition for light emitting diode (LED) materials is capable of being modified, so that the LED can be a light source which may produce different wavelengths and light colors. Hence, a multi-bandwidth light tube made by the LEDs is utilized to produce a certain amount of light at a specific wavelength incident on the plants, thereby controlling the plants growth per requirements.

Yet, the conventional multifunctional light emitting diode plant cultivation lamp for promoting growth rate has deficiencies as following:

First, the multi-bandwidth light tube is composed of a variety of LEDs with different wavelengths which is assembled into a specific order. Because the light emitting from the multi-bandwidth light tube is not entirely suitable for plants growth, and it does not take phytochrome, cryptochrome, phototropin, and photoperiod into considerations, the plant growth promotion is limited.

Second, it is unable to simulate natural sunlight for achieving a control over a light angle and a color temperature gradually, such that plant growth and flowering control is not precise.

SUMMARY OF THE INVENTION

The above deficiencies and problems associated with the conventional multi-bandwidth light tube are solved in accordance with certain aspects of the present invention. As per the aforementioned issues, the objective of the present invention is to provide a full spectrum sunshine simulation apparatus for developing biological growth which controls a color temperature variation, a photoperiod, and an incident angle of light emitted from a full spectrum light emitting diode to simulate natural sunlight, thereby achieving effect in modulating plant growth.

To achieve the aforementioned objectives, a technical proposal of the present invention is to provide a full spectrum sunshine simulation apparatus for developing biological growth, comprising: a main body; a full spectrum light emitting diode module, including a plurality of full spectrum light emitting diodes and a printed circuit board which is disposed on the main body firmly and is connected to the plurality of the full spectrum light emitting diodes; and a photoperiod controller, electrically connected to the printed circuit board for controlling the plurality of full spectrum light emitting diodes; wherein the luminescence spectrum of the plurality of full spectrum light emitting diodes has a wavelength range of 350 nm to 800 nm and the photoperiod controller is in charge of changing lighting periods of the plurality of full spectrum light emitting diodes, color temperatures and angles of the lights emitted from the full spectrum emitting diodes.

The present invention provides a full spectrum sunshine simulation apparatus for developing biological growth, comprising: a main body, a full spectrum light emitting diode module, including a plurality of full spectrum light emitting diodes and a printed circuit board which is disposed on the main body and electrically connected to the plurality of full spectrum light emitting diodes; a photoperiod controller, electrically connected to the printed circuit board, for controlling the plurality of full spectrum light emitting diodes, wherein the photoperiod controller includes: a processing unit, electrically coupled to a setup interface for generating a control signal; a memory unit, electrically coupled to the processing unit; a time unit, electrically connected to the processing unit and generating a time signal for triggering the processing unit to produce the control signal; and a driving unit, electrically connected to the processing unit and the full spectrum light emitting diode module and generated a driving signal in response to the control signal to control the plurality of full spectrum light emitting diodes; wherein the luminescence spectrum of the plurality of full spectrum light emitting diodes has a wavelength range of 350 nm to 800 nm and the photoperiod controller is in charge of changing lighting periods of the plurality of full spectrum light emitting diodes, color temperatures and angles of the lights emitted from the full spectrum emitting diodes.

To achieve the aforementioned objectives, a driving module of a photoperiod controller associated with a full spectrum sunshine simulation apparatus for developing biological growth according to the present invention is provided, comprising: a processing unit for generating a control signal; a memory unit, electrically connected with the processing unit; a time unit, electrically connected to the processing unit and generated a time signal for triggering the processing unit to produce the control signal; and a driving unit, electrically connected with the processing unit and the full spectrum light emitting diode module and generated a driving signal in response to the control signal to stimulate the full spectrum light emitting diode module; wherein the luminescence spectrum of the full spectrum light emitting diode module has a wavelength range of 350 nm to 800 nm and the driving signal controls a luminous period of the full spectrum light emitting diode module and modulates a color temperature and an emitting angle of the light emitted from the full spectrum light emitting diode module.

As per the aforementioned objectives, a driving method of a full spectrum sunshine simulation apparatus for developing biological growth is provided according to the present invention, comprising: supplying a time unit for generating a time signal; providing a processing unit for producing a control signal with respect to the time signal; and utilizing a driving unit, for generating a driving signal in response to the control signal to control a full spectrum light emitting diode module; wherein the full spectrum light emitting diode module has a wavelength range of 350 nm to 800 nm and the driving unit controls a lighting period of the full spectrum light emitting diode module, a color temperature and an emitting angle of the light emitted from the full spectrum light emitting diode module.

Consequently, the following efficacy of aforementioned technical proposal of the present invention is achieved:

The full spectrum sunshine simulation apparatus has a high illuminance and a larger luminous efficiency, so that the luminous intensity per hour incident on the plants increases so as to stimulate the plant growth and flowering.

Another full spectrum light emitting diode is capable of emitting light with a specific wavelength which is continuous and adjustable. It can simulate natural sunlight incident on the plants for photosynthesis and photoreceptor within the plants can absorb the light at a certain wavelength, thereby making appropriate adjustments for the plants physiologically.

A photoperiod controller is used to control the illumination duration of a full spectrum light emitting diode, regulate light exposure duration of the plants, and simulate a length of day daily through a year for stimulating and promoting the plant growth and flowering.

The photoperiod controller may use the full spectrum light emitting diode to regulate a color temperature variation of the light and simulate a natural sunshine color temperature daily so as to promote the plant growth.

Additionally, the photoperiod controller is used to modulate the full spectrum light emitting diode to produce different emitting light angles and simulate natural sunlight emitting angles daily for intimating a realistic natural environment.

In order to further understand the techniques, means and effects the present invention takes for achieving the prescribed objectives, the following detailed description and included drawings are hereby referred, such that, through which, the purposes, features and aspects of the present invention can be thoroughly and concretely appreciated; however, the included drawings are provided solely for reference and illustration, without any intention to be used for limiting the present invention, whose full scope and dimension is described only in the later following claims.

DETAILED DESCRIPTION OF THE PREFERRED EMBODIMENTS

Please refer to FIG. 2A, FIG. 2B, FIG. 2C, and FIG. 3, in which an embodiment of the full spectrum sunshine simulation apparatus for developing biological growth in accordance with certain aspects of the present technique is demonstrated. Provided is a full spectrum sunshine simulation apparatus for developing biological growth 1, adapted for promoting the plant growth, comprising a main body 10, a full spectrum light emitting diode module 20, and a photoperiod controller 30. In the embodiment, the main body 10 of the full spectrum sunshine simulation apparatus for developing biological growth 1 is a flat sheet shape device, but the shape of the main body 10 is not limited thereto. In another embodiment, the main body 10 is a box-shaped structure.

Figure 1:
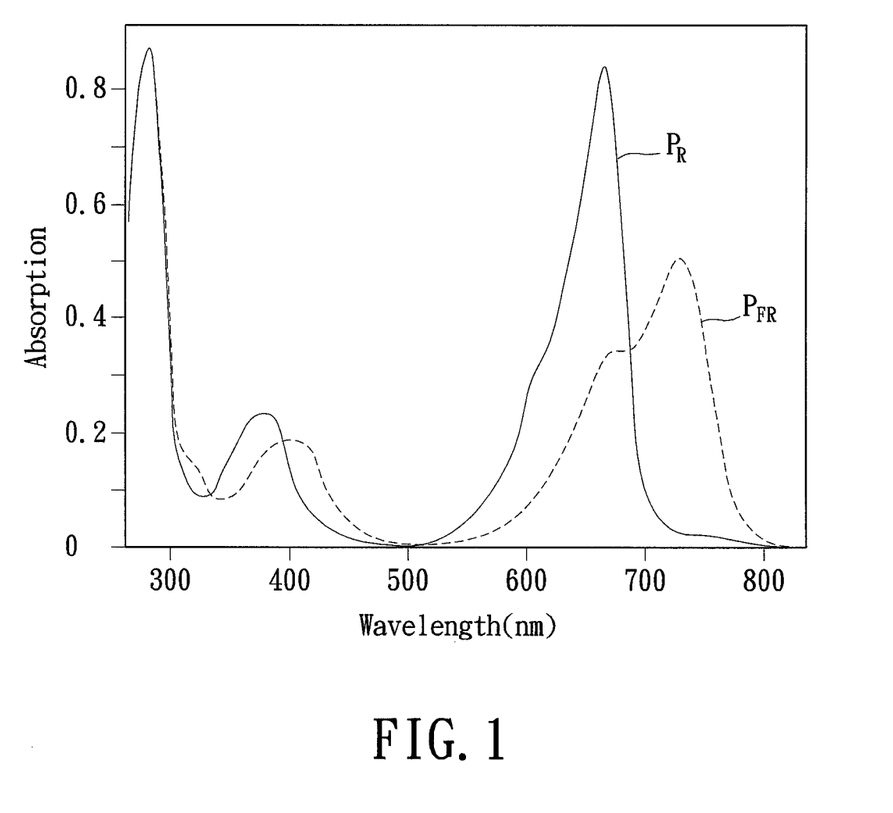
FIG. 1 illustrates a phytochrome absorption spectrum diagram in accordance with conventional plants.
Figure 2A:
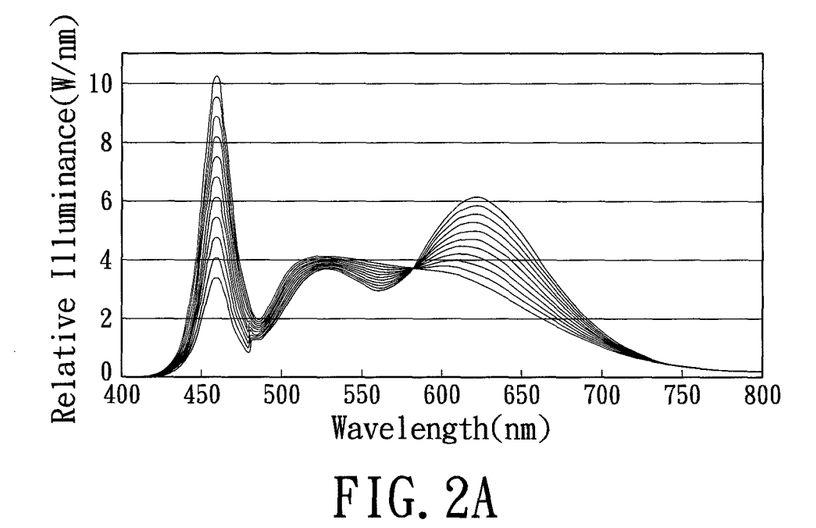
FIG. 2A illustrates a wavelength versus relative illuminance diagram of luminescence spectrum of a full spectrum light emitting diode in a color temperature range of 3,000 K to 6,500 K in accordance with certain aspects of the present technique.
Figure 2B:
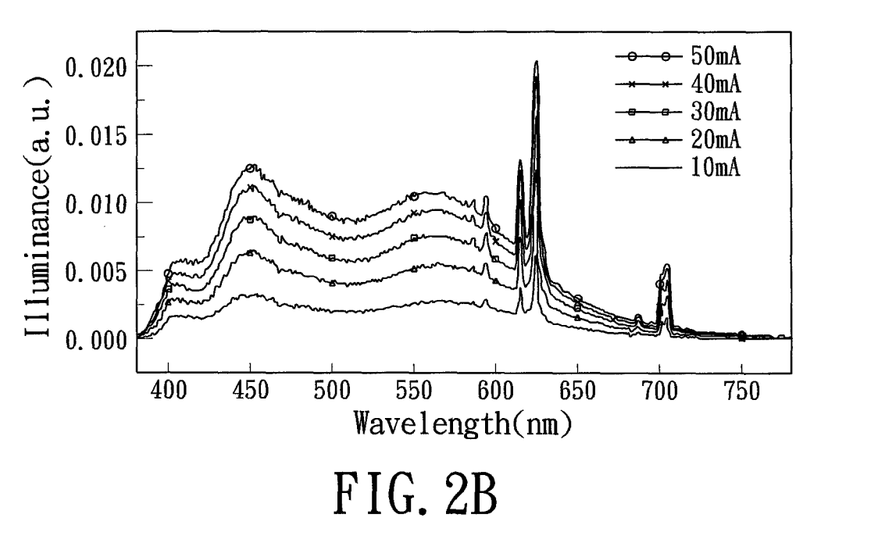
FIG. 2B illustrates a wavelength versus illuminance diagram of the full spectrum light emitting diode in accordance with certain aspects of the present technique.
Figure 2C:
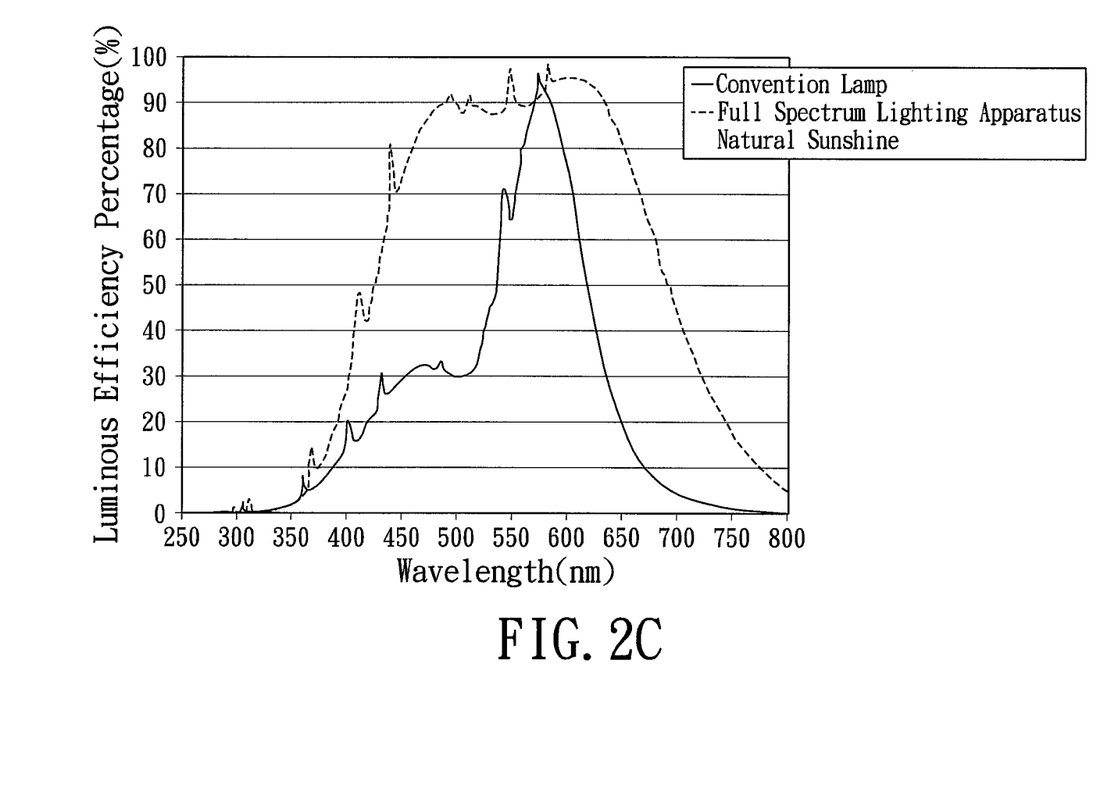
FIG. 2C illustrates a wavelength versus luminous efficiency percentage diagram of the full spectrum light emitting diode in accordance with certain aspects of the present technique.
Figure 3:
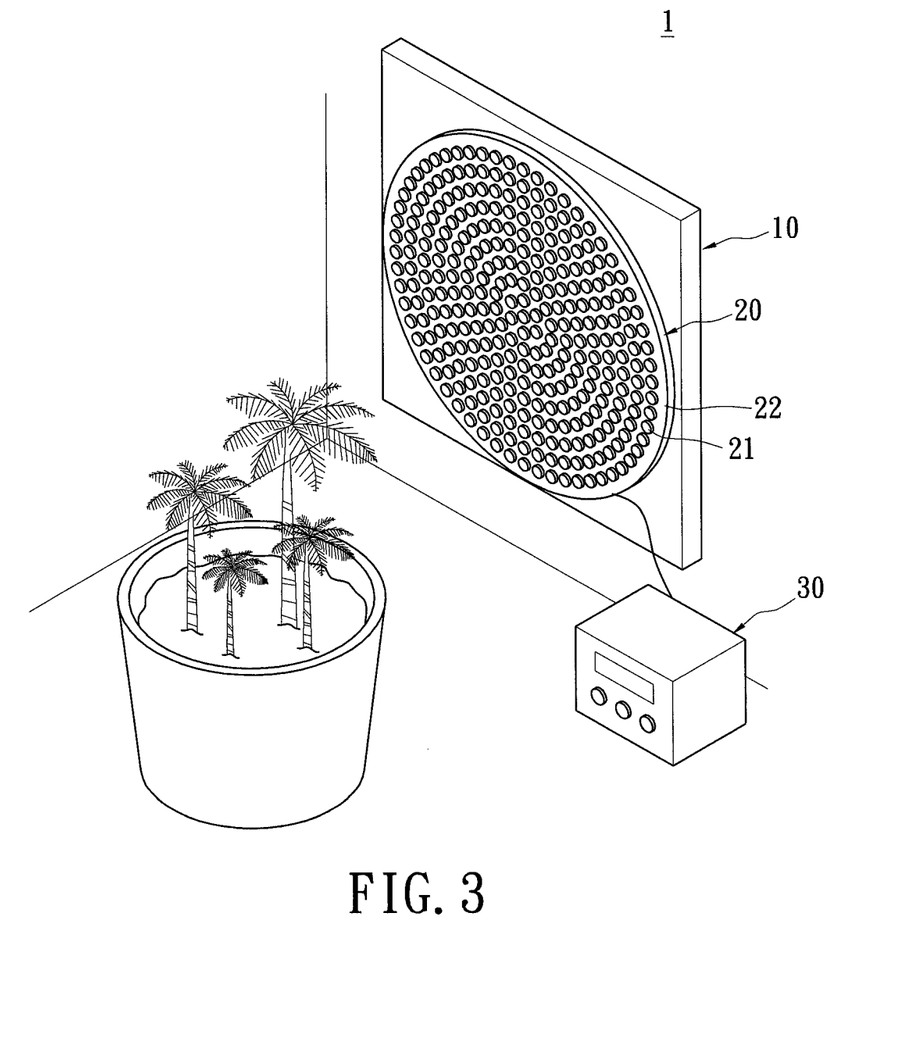
FIG. 3 illustrates a schematic diagram of the full spectrum sunshine simulation apparatus for developing biological growth according to the present invention.

The full spectrum light emitting diode module 20 is disposed on the main body 10 and includes a plurality of full spectrum light emitting diodes 21 disposed on the printed circuit board 22. The printed circuit board 22 is electrically connected to the full spectrum light emitting diodes 21. The full spectrum light emitting diodes 21 are composed of a plurality of white, blue, red, green, infrared, and ultraviolet LEDs, or different combinations of the above-mentioned LEDs in the wavelength range of 350 nm to 800 nm continuously as shown in FIG. 2A, FIG. 2B, and FIG. 2C. Therein, the continuous luminescence spectrum is corresponding to a phytochrome absorption diagram as shown in FIG. 1, wherein the luminescence spectrum has an ultraviolet light band, a blue light band, a green light band, a red light band, and an infrared light band. The ultraviolet light band and the blue light band have a wavelength range between 350 nm to 500 nm. The green light band has a wavelength range between 500 nm to 600 nm. The red light band has a wavelength range between 600 nm to 700 nm. The infrared light band has a wavelength range between 700 nm to 800 nm.

Therefore, the wavelength of light to stimulate the plants for photosynthesis is in the range of 350 nm to 800 nm, i.e., the ultraviolet light band, the blue light band, the green light band, and the infrared light band. Therefore, by controlling the emission light at a wavelength range of 350 nm to 800 nm, a natural sunlight is stimulated for promoting plant photosynthesis. Moreover, phytochrome can absorb a red light bandwidth and an infrared light bandwidth wave of the emission light and make appropriate adjustments for the plants physiologically. Additionally, crytochrome and phototropin respond to the wavelength of the emission light range between 350 nm to 800 nm in regulating many important physiological responses, wherein crytochrome and phototropin may absorb an ultraviolet light bandwidth and a blue light bandwidth wave from the emission light to support plant physiological responses in an appropriate fashion.

Furthermore, a minimum illuminance of the full spectrum light emitting diodes 21 is 5,000 Lux, wherein the preferred illuminance is between 10,000 Lux to 50,000 Lux as shown in FIG. 2B. High illuminance has larger luminous efficiency, thereby increasing the luminous intensity per hour incident on the plants, so that the required luminous intensity for developing plant growth and flowering in a daily basis is achieved easier.

The ultraviolet band and the blue band include a shorter wavelength region of the emission light with larger luminous efficiency; the infrared light band includes a longer wavelength region of the emission light with lower luminous efficiency. While the emission light includes different ratios of the ultraviolet light band, the blue light band, the green light band, the red light band, and the infrared light band, i.e., the emission light may have different luminous intensities and luminescent spectrums configured by a variety of combinations of wavelength bandwidths, so that different color temperature of the emission light is produced. The full spectrum light emitting diodes 21 according to the present invention may produce the emission light with a color temperature range from 3,000 K to 6,500 K as shown in FIG. 2A, wherein the color rendering index (CRI) exceeds 90. Additionally, the luminous efficiency percentage of the emission light from the full spectrum light emitting diodes 21 as shown in FIG. 2C is more close to that of the natural sunlight in contract to a common lighting lamp.

The photoperiod controller 30, electrically connected to the printed circuit board 22, controls the full spectrum light emitting diodes 21 to emit lights and to regulate the lighting duration of the full spectrum light emitting diodes 21, that is to regulate the illumination period of the full spectrum light emitting diode module 20 so as to modulate a light exposure time incident on the plants. Therefore, if a natural sunlight photoperiodism daily in four seasons (ex, spring, summer, fall, and winter) of a year can be simulated successfully, such that the plats have the appropriate length of day and night time, the plants development, growth, and flowering can be promoted. However, the photoperiodism is different for a variety of plants, e.g., long-day plants, such as spinach, lettuce, coreopsis, or delphinium. The photoperiod controller 30 controls the full spectrum light emitting diodes 21 to provide longer illumination period, i.e, summer, such that a flowering rate for the long-day plants increases; Regarding short-day plants, such as cosmos, chrysanthemum, or euphorbia pulcherrima, the photoperiod controller 30 controls the full spectrum light emitting diodes 21 to supply shorter illumination period, i.e., winter, such that a flowering rate of the short-day plants increase. Consequently, the photoperiod controller 30 may control illumination periods with respect to different plants in regulating the time and seasons for the plants growth and flowering.

It is worth to mention that the red light band from the emission light, e.g., 600 nm to 650 nm, may influence the ratio of light sensitive pigments (the ratio of phytochrome Pr and Pfr) in plants, thereby affecting the plants growth, development, and flowering. Crytochrome and phototropin are sensitive to the ultraviolet light band and the blue light band of the emission lights and are responsible for cruciferous plants such as *Arabidopsis* flowering growth control.

Moreover, the photoperiod controller 30 may regulate the color temperate variation of emission light out of the full spectrum light emitting diodes 21 in a range of 3,000 K to 6,500 K. For example, when a natural sunlight color temperature variation in a morning, noon, and night time is from 4,000 K to 6,000 K, and then to 3,000 K, the photoperiod controller 30 may modulate the color temperature of the emission light of the full spectrum light emitting diodes 21 changed from 4,000 K, to 6,000 K and then to 3,000 K, to simulate a sunlight color temperature in a whole day. The photoperiod controller 30 controls a ratio of luminous intensity and luminescence spectrum of the emission light from the full spectrum light emitting diodes 21, and incorporates the time to modulate the color temperature range within 3,000 K to 6,000 K, such that the plants are exposed under a natural environment with a appropriate color temperature, thereby promoting the plants development and growth.

Figure 4:
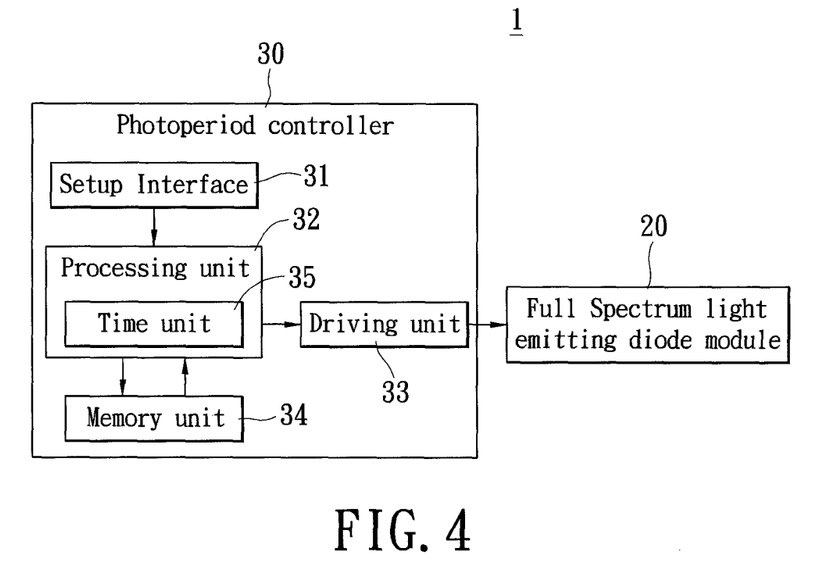
FIG. 4 illustrates a system block diagram of a photoperiod controller of the full spectrum sunshine simulation apparatus for developing biological growth according to the present invention.

Please refer to FIG. 4. The photoperiod controller 30 has a setup interface 31, a processing unit 32, a driving unit 33, a memory unit 34, and a time unit 35. Therein, the setup interface 31, the memory unit 24, and the driving unit 33 are electrically coupled to the processing unit 32. The driving unit 33 is electrically connected to the full spectrum light emitting diode module 20 and the time unit 35 is located within the processing unit 32.

The setup interface 31 provides an input interface for a user to input a setup value which includes an illumination period of the full spectrum light emitting diode module 20, a color temperature, an illuminance, and a light angle of the emission light. The setup value is stored into the memory unit 35 by the processing unit 32. The processing unit 32 may generate a control signal based on the setup value inputted by ways of the setup interface 31. The driving unit 33 receives the control signal and produces a driving signal to trigger the full spectrum light emitting diode module 20. The time unit 35 is disposed inside the processing unit 32 for producing a time signal. The processing unit 32 modulates the control signal in response to the time signal so as to control the illumination period of the full spectrum light emitting module 20, the color temperature, and light angle of the emission light. In practice, the processing unit 32 controls the full spectrum light emitting diode module 20 to simulate the color temperature variation and the illuminance of natural sunshine within a day from morning to night and in four seasons of a year. Thus, the user may setup a lighting period time thru the setup interface 21 larger or smaller than 24 hours, in other words, the user may freely regulate a day or a year time associated with the full spectrum sunshine simulation apparatus for developing biological growth 100, thereby slowing down or speeding up the process of plant growth.

Figure 5:
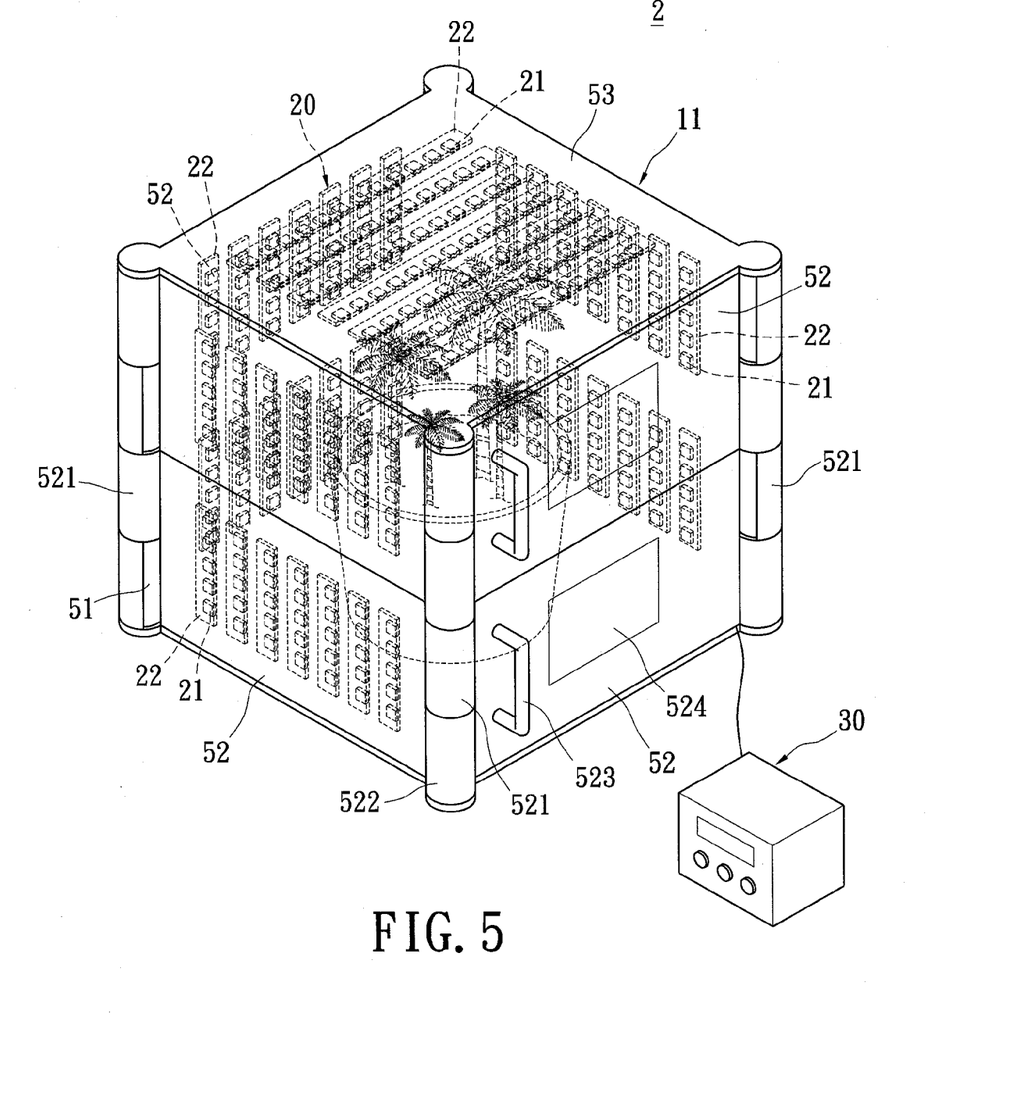
FIG. 5 illustrates a schematic diagram of another embodiment of the full spectrum sunshine simulation apparatus for developing biological growth according to the present invention.

Please refer to FIG. 5. A main body 11 of a full spectrum sunshine simulation apparatus for developing biological growth 2 may have different appearance designs. The main body 11 includes a frame 51, a plurality of side boards 52, and a top board 53, wherein the frame 51 surrounds the plant inside the main body 11. An area and a height of the frame 51 are designed according to the size of the plant. The plurality of side boards 52 may be assembled with the frames 51 and the top board 53 is disposed on the top of the frame 51. Each of the plurality of side boards 52 has a first fastening portion 521 and a second fastening portion 522. The first fastening portion 521 is disposed on an upper side of the side board 52 and the second fastening portion 522 is disposed on a lower side of the side board 52. As shown in FIG. 5, any two of the plurality of side boards 52 are incorporated with each other. The first fastening portion 521 and the second fastening portion 522 of each side board 51 are corresponding with the second fastening portion 522 and the first fastening portion 521 of adjacent side board 52. Therefore, the plurality of side boards 51 assembled with the frame 51 may enhance the expandability associated with the size and the height of the main body 11. The full spectrum light emitting diodes 21 and the printed circuit board 22 of the full spectrum light emitting diode module 20 are arranged uniformly on internal sides of the plurality of side boards 52 and a bottom surface of the top board 53. Furthermore, it may attach reflected light stickers (not shown) on the internal sides of the side boards 52 and on the bottom surface of the top board 53 for increasing illumination efficiency of the emission light. The side boards 52 may configure with a handle portion 523 and a window portion 524 which are utilized to observe the plant growth inside the main body 11 easier. Further, the side boards 52 may be made of a translucent, transparent, or a opaque material and may be a concealed, a half-concealed, or a closed environment.

Because the main body 11 of the full spectrum sunshine simulation apparatus for developing biological growth 2 of the embodiment according to the present invention may be a translucent or a transparent box which includes an internal space for the plant growth. This is also called a biological representation and development chamber which can modulate the illuminance of the full spectrum light emitting diode module 20, the color temperature, and light angle of the emission light by means of the photoperiod controller 30.

Moreover, because the full spectrum sunshine simulation apparatus for developing biological growth 2 of the embodiment with respect to the certain aspects of the present technique is a box structure, and the full spectrum light emitting diodes 21 are disposed on the peripheral section of the internal sides of the box to create as a environmental light source, the photoperiod controller 30 may control the illuminance of each of the side boards 52 and the top board 53 associated with the full spectrum light emitting diodes 21, the color temperature and the light angle of the emission light, so that the plants are able to be exposed under the emission lights from different directions. The embodiment of the present invention utilized the-above mentioned technical features to simulate a light angle variations in a day from morning to night, a color temperature modulation, and an illumination intensity change in four seasons of a year. Herein, the photoperiod controller 30 takes advantages of controlling the illumination sequence of the full spectrum light emitting diodes 21, thereby resulting in different effects in accordance with a variety of light angles. Hence, the full spectrum sunshine simulation apparatus for developing biological growth 2 of the present invention may simulate a realistic sunlight regarding its illuminance, illumination period, light angle, and color temperature change, so as to create a realistic natural environment for biological growth and development.

The photoperiod controller 30 may input a predetermined illumination period, an illumination intensity, and color temperature variation thru the setup interface 31, so that it may generate a control signal to control the driving unit 33 with respect to the tie signal provided by the processing unit 32 and the time unit 35. The driving unit 33 generates a driving signal to regulate the full spectrum light emitting diode module 20 in response to the control signal. At the same time, because the full spectrum sunshine simulation apparatus for developing biological growth 2 according to the present invention includes a surrounding light source, it may control the driving unit 33 thru the processing unit 32 to generate a artificial sunlight associated with it illuminance, light angle, and color temperature variation in a day from morning to night and in the four season of a year. Additionally, it may further input a point of Earth latitude and longitude associated with the intended simulation sunshine, such that a corresponding planetary motion data of the Earth with respect to the other plants of the Sun stored in the memory unit 34 incorporated with the point of Earth latitude and longitude are capable of calculating a corresponding illumination period, an illuminance, and a color temperature change of the position associated with the point of Earth latitude and longitude by the processing unit 32. Consequently, while a control signal generated from the processing unit 32 is utilized efficiently, the embodiment of the full spectrum sunshine simulation apparatus for developing biological growth 2 according to the present invention may simulate any one of sunshine environment on the Earth.

Figure 7:
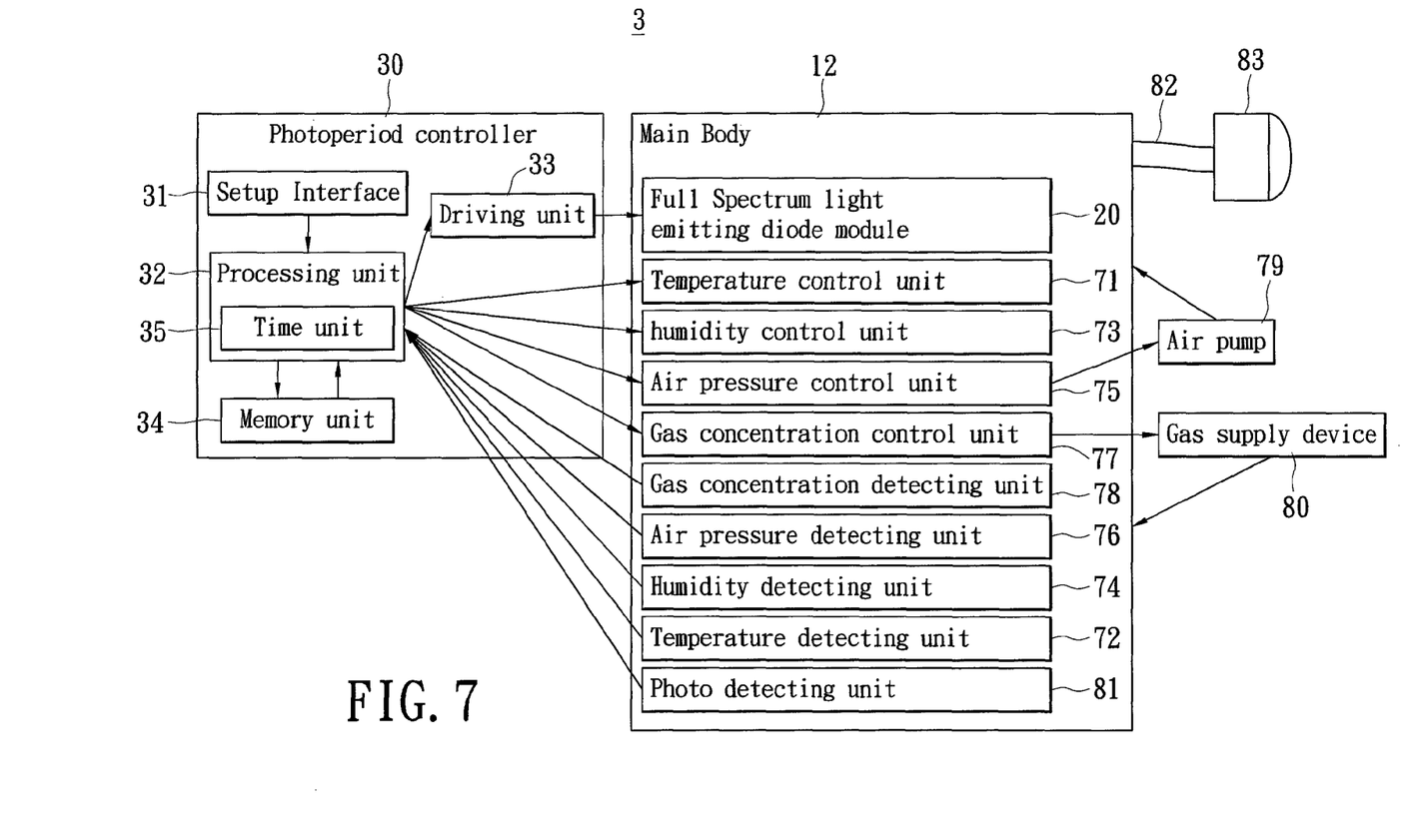
FIG. 7 illustrates a block diagram of the full spectrum sunshine simulation apparatus for developing biological growth according to the present invention.

Please refer to FIG. 7. Because the full spectrum sunshine simulation apparatus for developing biological growth 2 is capable of simulating a natural sunshine environment for any latitude and longitude position on the Earth, in another embodiment, a full spectrum sunshine simulation apparatus for developing biological growth 3 may additionally install a temperature control unit 71, a temperature detecting unit 72, a humidity control unit 73, a humidity detecting unit 74, a air pressure control unit 75, a air pressure detecting unit 76, a gas concentration control unit 77, a gas concentration detecting unit 78, a air pump 79, and a gas supply device 80. Wherein, the temperature control unit 71, the temperature detecting unit 72, the humidity control unit 73, the humidity detecting unit 74, the air pressure control unit 75, the air pressure detecting unit 76, the gas concentration control unit 77 and the gas concentration detecting unit 78 are electrically connected with the processing unit 32 of the photoperiod controller 30. Additionally, the air pump 70 is electrically connected to the air pressure control unit 75 and the gas supply device 80 is electrically connected to the gas concentration control unit 77.

Figure 6:
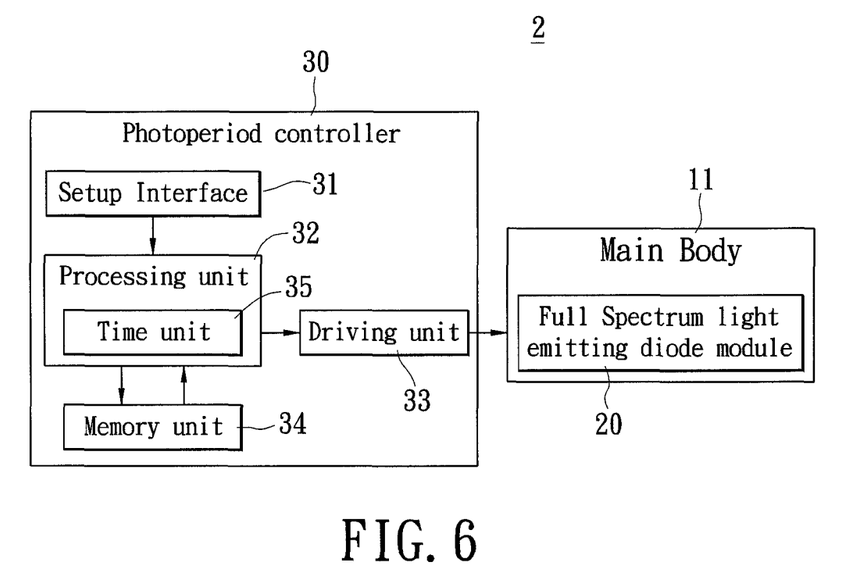
FIG. 6 illustrates a system block diagram of another embodiment of a photoperiod controller of the full spectrum sunshine simulation apparatus for developing biological growth according to the present invention.

Beside, the temperature detecting unit 72, the humidity detecting unit 74, the air pressure detecting unit 76, the gas concentration detecting unit 78, and a photo detecting unit 81 are disposed on the full spectrum sunshine simulation apparatus for developing biological growth 3 individually, so as to identify a temperature, a humidity, an atmosphere air pressure, a gas concentration for difference gases, an illuminance, and a color temperature associated with an internal environment of the full spectrum sunshine simulation apparatus for developing biological growth 3, respectively, and to generate each detecting signal correspondingly. The processing unit 32 receives the corresponding detecting signal and compares it to the setup value stored in the memory unit 34, so as to generate the control signal to regulate the full spectrum light emitting diode module 20, the temperature control unit 71, the humidity control unit 73, the air pressure control unit 75, and the gas concentration control unit 77 respectively, so that the objective in regulating the internal environment of the full spectrum sunshine simulation apparatus for developing biological growth 3 is achieved. Please refer to the aforementioned corresponding illumination period, the illuminance, and the color temperature change of the position associated with the point of Earth latitude and longitude in FIG. 6 and the technique that can regulate the illumination period, the illuminance, and the color temperature change of the full spectrum light emitting diode module 20 and simulate a color temperature for any latitude and longitude position on the Earth. Besides, it may eventually simulate a natural sunshine environment for any latitude and longitude position on the Earth in accordance with the atmosphere air pressure in different height and the temperature and humidity conditions. Consequently, according to the embodiment of the present technique, the full spectrum sunshine simulation apparatus for developing sunshine growth 3 may simulate a natural environment for any one Earth latitude and longitude position arbitrarily. In other words, any particular species in any specific position on the Earth may be developed easily based on the application of the full spectrum sunshine simulation apparatus for developing biological growth 3.

Therein, the air pressure control unit 75 controls the air pump 79 based on the control signal from the processing unit 32 to modulate an internal environmental air pressure inside the full spectrum sunshine simulation apparatus for developing biological growth. As a result, it may intimate air pressure status in the high mountain area. Except of that, the gas concentration control unit 77 controls the gas supply device 80 in response to the control signal of the processing unit 32. Because any individual species are suitable for a corresponding gas concentration or a specific gas concentration for living or development, the gas concentration unit 77 may control the gas supply device 80 for supplying a variety of gases with respect to the control signal of the processing unit 32, e.g., nitrogen, carbon dioxide, or oxygen, etc., such that a gas combination in the internal environmental of the main body 12 associated with the full spectrum sunshine simulation apparatus for developing biological growth may be regulated.

Moreover, the embodiment of the full spectrum light emitting diode module 20 according to the present invention has the luminescence spectrum within the ultraviolet band. The ultraviolet light spectrum band for the full spectrum sunshine simulation apparatus for developing biological growth 3 may has a special inhibitory function. Because the embodiment of the full spectrum sunshine simulation apparatus for developing biological growth 3 includes the full spectrum light emitting diode module 20 for providing sufficient light, the temperature control unit 71 and the humidity control unit 73 are used for supplying an appropriate growth temperature and humidity for species, the internal environment of the full spectrum sunshine simulation apparatus for developing biological growth 3 is especially designed for biological growth and development which also includes a variety of microorganisms and various fungi. However, while the microorganisms and fungi are excessive development, it may be harmful for other species in the main body 12 of the full spectrum sunshine simulation apparatus for developing biological growth 3. Hence, the ultraviolet light spectrum band in accordance with the present invention functions by inhabiting the development of microorganisms and fungi, such that the situation for overgrowing of microorganisms and fungi is prevented. The internal environment of the full spectrum sunshine simulation apparatus for developing biological growth 3 is maintained stably.

Consequently, in the embodiment of the present invention, the setup interface 31 of the photoperiod controller 30 is applied to input latitude and longitude point associated with the intended mimicked environment and height, etc. The processing unit 32 may combine the corresponding planetary motion data of the Earth with respect to the other plants of the Sun associated with other height and air pressure data to perform calculations and then generate a control signal. The processing unit 32 controls the full spectrum light emitting diode module 20 to produce a corresponding light angle, an illumination period, and a color temperature and it may simulate a temperature of a realistic environment by the temperature control unit 71, simulate a humidity of the realistic environment by the humidity control signal 73, and simulate a pressure change of the realistic environment by the air pressure control signal 75. Eventually, the full spectrum sunshine simulation apparatus for developing biological growth 3 which may mimic any positions on the Earth is proposed.

Therefore, because the full spectrum sunshine simulation apparatus for developing biological growth 3 simulates a natural biological growth environment successfully, it may be applied in either creating an appropriate biologically living environment on the Earth or manufacturing a biological pesticide. For example, an intended protected plant is disposed inside the full spectrum sunshine simulation apparatus for developing biological growth 3, and place a pest which is harmful for the protected plant in the artificial growth and development environment. Because the artificial environment is beneficial for the protected plant, the plants will be growing and is provided as food supply for the pest. At the same time, in the artificial environment, because the pest has no natural enemies with the presence of adequate food supply, the pest would breed. Then, place a predator of the pest in the artificial environment, the pest-eating predator will breed. Finally, while the predator of the pest reaches to the maximum propagation light, release the predators to the outside environment. Consequently, by applying the aforementioned biotechnological method, a biological pesticide is formed to replace chemical pesticides effectively.

Additionally, a light guide 82 may be applied to be electrically connected to the full spectrum sunshine simulation apparatus for developing biological growth 3. As per the characteristics of the light guide 82, the external environmental light is directed to the internal space of the main body 12. Herein, the light guide 82 may be disposed in the light collector 83, thereby collecting natural sunshine of the external environment and then directing into the main body 12 thru the light guide 82. The light detecting unit 81 senses a combination of the natural sunlight from the light guide 82 and the illuminance and color temperature emitted from the full spectrum light emitting diode module 20 to produce a detecting signal. The processing unit 32 responses to the detecting unit to regulate the illuminance and color temperature of the full spectrum light emitting diode module 20, so that the main body 12 may be maintained in a stable setup environment.

It is worth to mention that, as per the aforementioned embodiment, the full spectrum light emitting diodes for the full spectrum light emitting diode module are applied and illustrated for example, but not limited thereto. The person skilled in the ordinary art, the full spectrum light emitting diode module may be composed of a plurality of full spectrum illumination devices, e.g., full spectrum fluorescent tubes or bulbs; in other words, the full spectrum illumination devices may be made of full spectrum light emitting diodes, full spectrum fluorescent tubes or bulbs.

In the aspects of the aforementioned embodiments, the technical characteristics of the present invention are as flowing:

The full spectrum light emitting diodes 21 have high illuminances and larger luminous efficiencies, so that the luminous intensity per hour incident on the plants increases so as to stimulate the plant growth and flowering.

The full spectrum light emitting diodes 21 are capable of emitting lights with specific wavelengths which are continuous and adjustable. It can simulate natural sunlight incident on the plants for photosynthesis and photoreceptor within the plants can absorb the lights at certain wavelengths, thereby making appropriate adjustments for the plants physiologically.

A photoperiod controller 30 is used to control the illumination duration of the full spectrum light emitting diodes 21, regulate light exposure duration of the plants, and simulate a length of day daily through a year for stimulating and promoting the plant growth and flowering.

The photoperiod controller 30 may use the full spectrum light emitting diodes 21 to regulate a color temperature variation of the light and simulate a natural sunshine color temperature daily so as to promote the plant growth.

Additionally, the photoperiod controller is used to modulate the full spectrum light emitting diode to produce different emission light angles and simulate natural sunlight angles daily for intimating a realistic natural environment.

The main body 10, 11, and 12, can expand the size and height of the main body 10, 11, 12, thereby enhancing the convenience in use.

The aforementioned descriptions represent merely the preferred embodiment of the present invention, without any intention to limit the scope of the present invention thereto. Various equivalent changes, alterations, or modifications based on the claims of present invention are all consequently viewed as being embraced by the scope of the present invention.

What is claimed is:

1. A full spectrum sunshine simulation apparatus for developing biological growth, comprising:
   a main body;
   a full spectrum light emitting diode module, including a plurality of full spectrum light emitting diodes and a printed circuit board which is disposed on the main body firmly and is connected to the plurality of the full spectrum light emitting diodes;
   a photoperiod controller, electrically connected to the printed circuit board for controlling the plurality of full spectrum light emitting diodes; and
   a light guide for allowing an external light transmitting to the main body, a photo detecting unit, and the full spectrum light emitting diode module, so as to control an illuminance and a color temperature of an internal environment of the main body;
   wherein the photoperiod controller is in charge of changing lighting periods of the plurality of full spectrum light emitting diodes, color temperatures and angles of the diodes emitted from the full spectrum emitting diodes, and includes:
   a processing unit for generating a control signal;
   a memory unit, electrically connected with the processing unit;
   a time unit, electrically connected to the processing unit and generating a time signal for triggering the processing unit to produce the control signal;
   a driving unit, electrically connected to the processing unit and the full spectrum light emitting diode module and generating a driving signal in response to the control signal to control the plurality of full spectrum light emitting diodes; and
   a setup interface for providing to a user the input of a setup value wherein the setup value is stored in the memory unit;
   wherein the memory unit further stores a corresponding planetary motion data of the earth with respect to the other planets of the solar system.

2. The full spectrum sunshine simulation apparatus for developing biological growth as claimed in claim 1, wherein the plurality of full spectrum light emitting diodes have a luminescence spectrum ranging from 350 nm to 800 nm.

3. The full spectrum sunshine simulation apparatus for developing biological growth as claimed in claim 1, wherein the plurality of full spectrum light emitting diodes emits lights having color temperatures in a range of 3,000 K to 6,000 K.

4. The full spectrum sunshine simulation apparatus for developing biological growth as claimed in claim 1, wherein an illuminance of the plurality of full spectrum light emitting diodes is in a range of 5,000 to 50,000 Lux.

5. The full spectrum sunshine simulation apparatus for developing biological growth as claimed in claim 1, wherein the main body is a box-shaped structure.

6. The full spectrum sunshine simulation apparatus for developing biological growth as claimed in claim 1, wherein the photoperiod controller manages the illuminating sequence of the plurality of full spectrum light emitting diodes so as to generate different illuminating angles.

7. The full spectrum sunshine simulation apparatus for developing biological growth as claimed in claim 1, further including: a temperature detecting unit, electrically connected to the processing unit; a temperature control unit, electrically connected to the processing unit; a humidity detecting unit, electrically connected to the processing unit; and a humidity control unit, electrically connected to the processing unit; wherein the processing unit controls the temperature control unit and the humidity control unit respectively, for processing adjustments in a temperature and a humidity of an internal environment of the full spectrum sunshine simulation apparatus for developing biological growth, based on individually detected results of the temperature detecting unit and the humidity detecting unit.

8. The full spectrum sunshine simulation apparatus for developing biological growth as claimed in claim 7, further comprising: a air pressure detecting unit, electrically connected to the processing unit; a air pressure control unit, electrically connected to the processing unit; a gas concentration detecting unit, electrically connected to the processing unit; and a gas concentration control unit, electrically connected to the processing unit; wherein the processing unit controls the air pressure control unit and the gas concentration control unit respectively, for processing adjustments in a air pressure and a gas concentration of the internal environment of the full spectrum sunshine simulation apparatus for developing biological growth, based on individually detected results of the air pressure detecting unit and the gas concentration detecting unit.

9. A driving module of a photoperiod controller associated with a full spectrum sunshine simulation apparatus for developing biological growth, adapted for controlling a full spectrum light emitting diode module, comprising:
   a processing unit for generating a control signal;
   a memory unit, electrically connected with the processing unit;
   a time unit, electrically connected to the processing unit and generating a time signal for triggering the processing unit to produce the control signal;
   a driving unit, electrically connected to the processing unit and generating a driving signal in response to the control signal to stimulate the full spectrum light emitting diode module; and
   a setup interface which is allowed to input a setup value stored it in the memory unit by the processing unit;
   wherein the driving signal controls a luminous period of the full spectrum light emitting diode module and modulates a color temperature and an emitting angle of the light emitted from the full spectrum light emitting diode module, and the memory unit stores a corresponding planetary motion data of the earth with respect to the other planets of the solar system.

10. The driving module as claimed in claim 9, wherein the full spectrum light emitting diode is composed of a plurality of full spectrum light emitting diodes.

11. A driving method of a full spectrum sunshine simulation apparatus for developing biological growth, comprising:
   a time unit for generating a time signal;
   a processing unit for producing a control signal with respect to the time signal;
   a driving unit, for generating a driving signal in response to the control signal to control a full spectrum light emitting diode module;
   a light guide for allowing an external light transmitting to the main body, a photo detecting unit, and the full spectrum light emitting diode module, so as to control an illuminance and a color temperature of an internal environment of the main body; and
   a memory unit which stores a corresponding planetary motion data of the earth with respect to the other planets of the solar system; and a setup interface, for inputting a setup value and storing it into the memory unit by the processing unit;
wherein the processing unit generates the control signal according to the stored date of the memory unit, and the full spectrum light emitting diode module has a wavelength range of 350 nm to 800 nm and the driving unit controls a lighting period of the full spectrum light emitting diode module, a color temperature and an emitting angle of the light emitted from the full spectrum light emitting diode module.

* * * * *